(12) United States Patent
Birkel et al.

(10) Patent No.: US 7,455,832 B2
(45) Date of Patent: *Nov. 25, 2008

(54) COSMETIC PREPARATION IN GEL FORM

(75) Inventors: Susanne Birkel, Glashuetten (DE); Juergen Allwohn, Burgschwalbach (DE); Harald Wendel, Ober-Ramstadt (DE); Michael Franzke, Rossdorf (DE); Birgit Schreiber, Lindenfels (DE); Axel Kalbfleisch, Darmstadt (DE)

(73) Assignee: Wella AG, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/989,914

(22) Filed: Nov. 16, 2004

(65) Prior Publication Data

US 2005/0123495 A1 Jun. 9, 2005

(51) Int. Cl.
*A61Q 5/00* (2006.01)

(52) U.S. Cl. ............... 424/70.16; 424/70.11; 424/70.15

(58) Field of Classification Search ....................... None
See application file for complete search history.

(56) References Cited

U.S. PATENT DOCUMENTS 4,459,285 A * 7/1984 Grollier et al. ............... 424/74

5,032,391 A * 7/1991 Helioff et al. ............ 424/70.15
6,358,493 B1 * 3/2002 Birkel et al. ................... 424/43
6,623,727 B2 * 9/2003 Birkel et al. ............... 424/70.1
7,083,810 B2 * 8/2006 Birkel et al. ................. 424/702

FOREIGN PATENT DOCUMENTS

| WO | WO 92/07011 | * | 4/1992 |
| WO | 92/13513 | | 8/1992 |
| WO | 95/07803 | | 3/1995 |
| WO | 96/14054 | | 5/1996 |
| WO | 98/58688 | | 12/1998 |
| WO | WO 01/03658 | * | 1/2001 |

OTHER PUBLICATIONS

Harry's Cosmeticology by Ralph Harry, pp. 470-473 (1982).*
JP -62091577 (Abstract) Apr. 1987.*
International Cosmetic Ingredient Dictionary and Hadbook, Ninth Edition 2002, vol. 4, Published by the Cosmetic, Toiletry and Fragrance Association, Washington, D.C., pp. 2920-2922 (in English).

* cited by examiner

*Primary Examiner*—Jyothsna A Venkat
(74) *Attorney, Agent, or Firm*—Michael J. Stricker

(57) ABSTRACT

A cosmetic preparation in gel form is described which contains undissolved, water-swollen polymer particles and at the interface with gaseous substances forms reversibly a grainy, uneven, light-scattering surface and at the interface with solids forms reversibly a smooth, level, non-light-scattering surface. Preferred gel formers are superabsorbing polymers. A preferred use is the hair-end protection in permanent wave treatment.

9 Claims, 3 Drawing Sheets

COSMETIC PREPARATION IN GEL FORM

CROSS-REFERENCES

The present invention described and claimed below is also described in U.S. patent application Ser. No. 10/018,933, which is the U.S. National Stage of PCT/EP 01/04024, which was filed on Apr. 7, 2001, in Europe, which, in turn, is based on German Application 100 19 314.5, filed in Germany on Apr. 19, 2000. A claim of priority of invention for the invention described and claimed hereinbelow is based on the foregoing U.S. patent application Ser. No. 10/018,933, under 35 U.S.C. 120, and also on German Patent Application 100 19 314.5 under 35 U.S.C. 119 (a) to (d).

BACKGROUND OF THE INVENTION

The object of the invention is a cosmetic preparation in the form of a gel having special consistency and with a particular surface appearance. The gel contains undissolved, gelled, water-swelled polymer particles and at the interface with gaseous substances forms reversibly a grainy, uneven, light-scattering surface and at the interface with solids it forms reversibly a smooth, level, non-light-scattering surface. Preferred gel formers are superabsorbing polymers. Another object of the invention is the use of superabsorbing polymers for hair-end protection during permanent wave treatments.

To confer strength and hold to human hair or to stabilize an established hair style, hair-treatment preparations in the form of, for example, gels, liquid gels, spray gels etc. are used. As a rule, such products contain a combination of gel formers and hair-fixing polymers. The cosmetic, hair-fixing polymers used for this purpose exhibit good fixing properties in aqueous, alcoholic or aqueous-alcoholic media and after application keep the hair more or less in shape and fix it and stabilize the established hair style. The drawback of conventional hair gels is that they require a relatively high content of gel formers. This results in higher formulation costs and a higher risk of incompatibility with other formulation constituents as well as in undesirable side effects on the hair, for example, stickiness, higher build-up etc.

The object of the invention is to provide cosmetic preparations with, on the one hand, novel, unusual properties, particularly a novel external appearance or a novel consistency and, on the other, to avoid the aforesaid drawbacks of conventional gels, such preparations retaining or even improving the special properties such as hair fixing and hair structuring, gel look, or wet look. A characteristic property of a gel is, for example, its surface condition. The novel, unusual properties are, at any rate, intended not to reduce substantially the cosmetic effects but, ideally, even to enhance them.

To produce a permanent deformation of human hair, curlers are needed in addition to reducing agents and oxidants. The hair is wound up along its longitudinal axis from the hair ends to the root region near the scalp. The repeated twisting of the hair around the curler causes the hair ends to have a necessarily smaller curl than does the root region. The hair-end deformation resulting in a small curl, however, hinders hair styling and is undesirable. This situation is aggravated by the fact that hair in the undamaged (natural) state of the root region has an even more closed cuticula. As a result, the root region is more resistant than the end region which is months older and as a result of the effect of combing, washing, bleaching, dyeing or waving and of environmental effects becomes increasingly brittle and more permeable. The aforementioned drawbacks concerning the hair ends result in a deterioration of the structure and stylability.

Repeated attempts have been made to achieve uniform waving, end protection or structure balancing by means of permanent wave pretreatment agents (for example, WO 07/09028) or with end paper impregnated with an acid (for example DE 33 11 292 A and DE 1 492 007 A) or with oil (for example DE 42 36 726 A). End paper impregnated with acid or oil shows only a weak effect as far as wave and structure balancing is concerned.

SUMMARY OF THE INVENTION

The object of the present invention is to prevent the above-said overcurling effect to a higher degree so that during exposure to the waving preparation the lengths and ends are spared in unusual fashion compared to the conventional procedure the known drawbacks thus being avoided. In this manner, less damage will be done to the hair structure and, despite tighter winding, the lengths and ends will have a wave radius comparable to that of the root regions close to the scalp.

We have now found that this objective can be reached by means of a cosmetic preparation in gel form, particularly a hydrogel, which contains undissolved, gelled, water-swollen polymer particles. For purposes of the invention, undissolved polymer particles are particles which in contrast to conventional gel formers (see FIG. 3/3) do not dissolve even in the swollen state, but form solid, discrete gel entities (see FIGS. 1/3 and 2/3). The gel of the invention forms at the interface with gaseous substances reversibly a grainy, uneven, light-scattering surface (see FIG. 1/3) and at the interface with solid substances reversibly a smooth, even, non-light-scattering surface (see FIG. 2/3). To form the gel structure, water-swellable and water-absorbing polymers, particularly super-absorbing polymers, are preferably used. On contact with water or aqueous solutions, superabsorbing polymers form swollen, gelled particles which in the gel of the invention are present in dispersed or associated form. Super-absorbing polymers are known from their use in absorbing sanitary products, such as diapers, products used for adult incontinence, female hygiene and wound dressing. They can be defined as water-insoluble, crosslinked polymers which while gelling to form hydrogels can absorb a multiple of, namely up to 1000 times, their weight of aqueous liquids and retain the absorbed amount of liquid under pressure.

Another object of the invention is the use of superabsorbing polymers for hair-end protection during permanent wave treatments. Surprisingly, we have found that the undesirable excessively tight curling of the hair ends can be prevented by use of superabsorbing polymers for hair-end protection. At the same time, the sensitive part of the hair is protected by the gel, and excessive swelling is prevented by local dilution of the waving liquid. By use of the cosmetic preparation in gel form, it was possible to obtain a uniform wave appearance even on previously damaged hair.

Still another object of the invention is a hair-treating preparation in the form of a gel containing water-swollen particles of a water-absorbing, particularly superabsorbing polymer.

In a particular embodiment of the invention, the hair-treating preparation is a hair-styling or hair-care preparation containing (A) at least one superabsorbing polymer and
(B) at least one second polymer selected from the group consisting of hair-fixing polymers and hair-care polymers, wherein the superabsorbing polymer (A) is preferably present in the form of undissolved, water-swollen, gelled particles.

The gels of the invention are characterized by their unusual external appearance and consistency. Preferably, the gelled particles have an average diameter of less than or equal to 2000 μm, particularly from 20 to 2000 μm and most preferably from 40 to 1400 μm. The particle size can readily be determined by scaled microphotography in either reflected or transmitted light (see FIGS. 1/3 and 2/3).

DETAILED DESCRIPTION OF THE INVENTION

Figure 1:
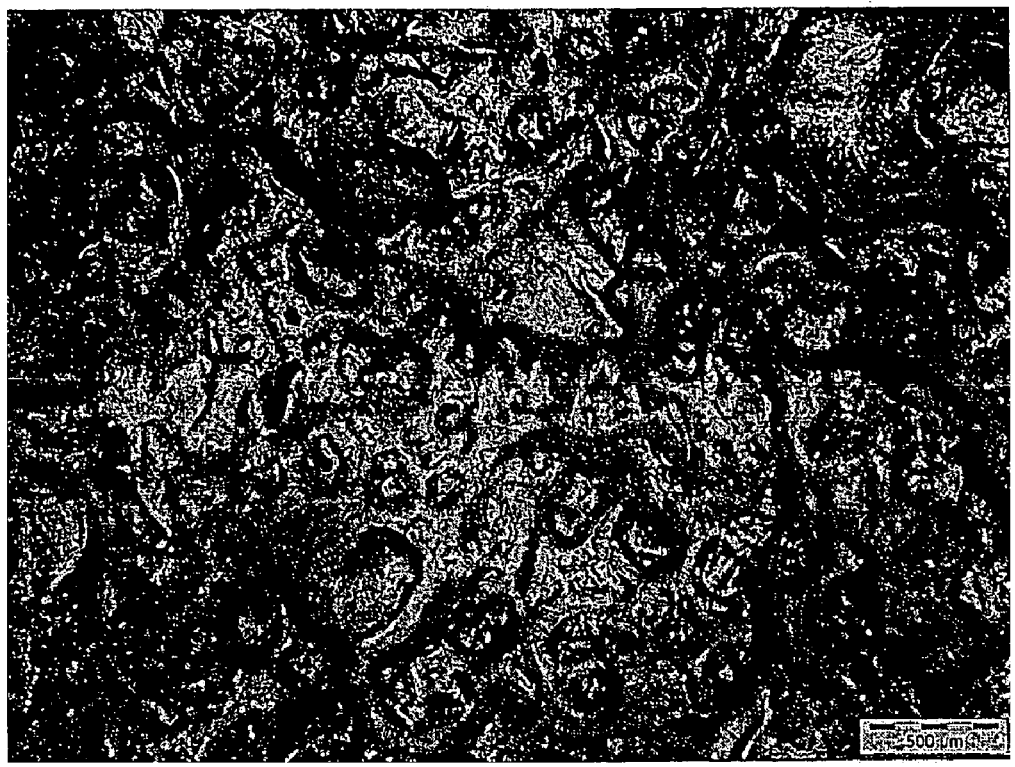
FIG. 1/3 shows a photograph of the surface of a gel of the invention (Example 2) taken in reflected light (lens 2.5×). The gel is resting on a specimen slide.

The superabsorbing polymers used according to the invention are known from their use as absorbers of liquids, for example in diapers. Usually, they are polymers or hydrophilic copolymers of acrylic acid or methacrylic acid, or they are graft copolymers of starch and acrylic acid, the polymers possibly being neutralized or partly neutralized as salts. Said polymers are formed by polymerization and partial cross-linking with appropriate crosslinkers derived from ethylenically unsaturated hydrophilic monomers, particularly acrylic acid, methacrylic acid or the alkali metal salts thereof. Such polymers and their preparation have been described often, for example in EP 0 312 952, DE44 18 818 and EP 0 441 507.

Particularly preferred are superabsorbing sodium polyacrylates. The superabsorbing polymers are characterized by their high water-absorption capacity and their high water retention. They are commercially available in powder or granular form. Suitable superabsorbing polymers are, for example, AQUA-KEEP® (Elf Atochem S.A.), Sanwet® IM 7015 (BASF AG), Sanwet® 3746-5 (BASF AG), Hysorb® E1290-00 (BASF AG), Hysorb® E 1291-00 (BASF AG) or Norsocryl XFS (Elf Atochem). The average particle size of the dry polymers is preferably from 100 to 850 μm. Particularly preferred are smaller particles of 200 μm and lower. The absorption capacity for demineralized water (centrifuge retention capacity) is preferably at least 20 g/g. The superabsorbing polymers are preferably present in an amount from 0.05 to 20 wt. % and particularly from 0.1 to 2 wt. % and preferably are the only gel formers of the gel of the invention. For permanent wave pretreatment, the superabsorbing polymers are preferably used in an amount from 0.1 to 5 wt. % and particularly from 0.5 to 2wt. %.

The second polymer (B) contained in the preferred embodiment is preferably present in an amount from 0.1 to 30 wt. % and particularly from 0.5 to 15 wt. %. The second polymer (B) is selected from the group consisting of hair-care and hair-fixing polymers. This polymer can be nonionic, anionic, cationic or zwitterionic, i.e., amphoteric. Nonionic polymers are particularly preferred. Said polymers can be synthetic or natural. By natural polymers are also meant chemically modified polymers of natural origin. Particularly preferred are polymers having sufficient solubility or dispersibility in water, alcohol or water-alcohol mixtures so that in the preparation of the invention they may exist in dissolved or homogeneously dispersed form. According to the invention, by hair-fixing polymers are meant polymers which when used in a 0.01 to 5% aqueous, alcoholic or aqueous-alcoholic solution are capable of depositing a polymer film onto the hair. By hair-care polymers are meant polymers that show substantivity and accumulate on the hair, and in this manner exert a cosmetic effect on the hair, for example by improving the combability, feel or luster of the hair.

Film-forming, hair-fixing nonionic polymers are particularly preferred for use in the gel of the invention. In contrast to ionic polymers, nonionic polymers have better compatibility with superabsorbing polymers within a wide range. Suitable nonionic polymers are the homopolymers and copolymers derived from at least one of the following monomers: vinylpyrrolidone, vinylcaprolactam, vinyl esters such as, for example, vinyl acetate, vinyl alcohol, acrylamide, methacrylamide, alkyl and dialkylacrylamide, alkyl and dialkylmethacrylamide, alkyl acrylate, alkyl methacrylate, propylene glycol or ethylene glycol, the alkyl groups of these monomers preferably being $C_1$-$C_7$-alkyl group and particularly $C_1$-$C_3$-alkyl groups. Suitable are, for example, the homopolymers of vinylcaprolactam, vinylpyrrolidone or N-vinylformamide. Other suitable synthetic, film-forming, nonionic, hair-fixing polymers are, for example, the copolymers of vinylpyrrolidone and vinyl acetate, the terpolymers of vinylpyrrolidone, vinyl acetate and vinyl propionate, polyacrylamides, for example those sold by CHEM-Y Emmerich under the tradename Akypomino® P 191 and by Seppic as Sepigel® 305; furthermore, polyvinyl alcohols sold, for example, by Du Pont under the tradename Elvanol® or by Air Products under the tradename Vinol® 523/540, and polyethylene glycol/polypropylene glycol copolymers sold, for example, by Union Carbide under the tradename Ucon®. Particularly preferred are polyvinylpyrrolidone, polyvinylcaprolactam and the copolymers obtained with at least one additional nonionic monomer, particularly polyvinylpyrrolidone/vinyl acetate copolymers.

The gel of the invention is preferably produced in an aqueous or aqueous-alcoholic medium with preferably up to 30 wt. % of alcohol. An alcohol content of 15 to 20 wt. % is particularly preferred.

In this case, the use of preservatives may advantageously be omitted. Suitable alcohols are, in particular, the lower alcohols with 1 to 4 carbon atoms commonly used for cosmetic purposes, for example ethanol and isopropanol. The preparation of the invention can have a pH in the range from 2.0 to 9.5, a pH in the range from 2.5 to 8 being particularly preferred. Suitable additional cosolvents are organic solvents or a mixture of solvents with a boiling point below 400° C., used in an amount from 0.1 to 15 wt. % and preferably from 1 to 10 wt. %. Particularly suitable as additional cosolvents are glycerol, ethylene glycol, propylene glycol and polyethylene glycols, used in an amount of up to 30 wt. %.

Optionally, the consistency of the gel of the invention can be optimized by using other common thickeners or gel-formers. Suitable for this purpose are, for example, the carboxyvinyl polymers, particularly the polyacrylates, for example the various Carbopol types, moreover polyglycols, cellulose derivatives, particularly hydroxyalkylcelluloses, and alginates, carrageenan, and inorganic thickeners, for example natural or synthetic bentonites. The additional gel formers and thickeners are typically used at a concentration from about 0.2 to 3.0 wt. % and preferably from 0.2 to 1 wt. %.

The preparation of the invention can also contain additives commonly used in hair-treatment preparations, for example wetting agents or emulsifiers belonging to the classes of nonionic, anionic, cationic or amphoteric surfactants, such as the ethoxylated or nonethoxylated fatty alcohol sulfates, alkylbenzenesulfonates, alkyltrimethylammonium salts, or alkylbetaines, in an amount from 0.1 to 15 wt. %, moisturizers, perfume oils in an amount from 0.1 to 0.5 wt. %, opacifiers, for example ethylene glycol distearate, in an amount from about 0.2 to 5.0 wt. %, pearly luster-imparting agents, for example a mixture of fatty acid monoalkylolamide and ethylene glycol distearate, in an amount from about 1.0 to 10 wt. %, bactericides and fungicides, for example 2,4,4-trichloro-2-hydroxydiphenyl ether or methylchloroisothiazolidone, in an amount from 0.01 to 1.0 wt. %, buffers, for example sodium citrate or sodium phosphate, in an amount from 0.1 to 1.0 wt. %, tinting agents, for example sodium fluorescein, in an amount form about 0.1 to 1.0 wt. %, hair-care agents, for example plant and herb extracts, protein hydrolyzates, silk hydrolyzates and lanolin derivatives, in an amount from 0.1 to 5 wt. %; physiologically tolerated silicone derivatives, for example volatile and nonvolatile silicone oils or high-molecular-weight siloxane polymers, in an amount from 0.05 to 20 wt. %; light protection agents, antioxidants, radical scavengers, antidandruff agents, in an amount from about 0.01 to 2 wt. %; fatty alcohols, luster-imparting agents, vitamins, softeners combability improvers, regreasing agents and defoamers.

The viscosity of the gel of the invention at 25° C. is preferably from 500 to 3000 mPa s and more preferably from 1000 to 1500 mPA s (measured at a temperature of 25° C. and a shear gradient of 0.5 to 1400 $s^{-1}$ with the RheoStress 100 rotational viscometer supplied by Haake).

For use as hair-end protectors during permanent wave treatments, the described gels can be applied to the hair ends directly by means of a brush or spatula. The application of gel extruded from a tube is also practicable. As an alternative, the hair ends can be dipped into the gel or pulled over the gel so as to ensure the adherence of a sufficient amount of gel. To the hair ends in the hair strands arranged for permanent waving is applied from 0.5 to 5 g and preferably from 0.8 to 3 g of gel. Liquid-permeable foils or end papers can be used as adjuvants. The foils or end papers impregnated or coated with the gel of the invention are also an object of the invention. Foils such as end papers for permanent waving are in themselves known. Usually, they consist of wet-strength paper, for example long-fiber paper, tissue paper or Japan paper. The foil, however, can also consist of some other absorbent material, for example, nonwoven material, cotton tissue or tissue derived from blends of synthetic and natural fibers. The gel can also be applied to the foil or end paper in the manner described hereinabove for hair.

Comparative experiments performed on test subjects and in which only common end paper was used resulted in appreciably weaker, less uniform and, hence, unsatisfactory results thus confirming the above-described effects in a very impressive manner.

The following examples illustrate the object of the invention in greater detail. The polymer contents given in the examples always refer to the solids content.

EXAMPLES

Example 1

Cooling Cosmetic Preparation

| | |
|---|---|
| 0.5 g | of Sanwet ® 3746-5 (BASF, superabsorbing sodium polyacrylate) |
| 0.2 g | of menthol |
| 20 g | of ethanol |
| to 100 g | water |

Example 2

Hair Gel

| | |
|---|---|
| 0.7 g | of Sanwet ® 3746-5 (BASF, superabsorbing sodium polyacrylate) |
| 10 g | of Luviskol ® VA 64 (BASF, PVP/VA[1] copolymer) |
| 0.2 g | of PEG-40 hydrogenated castor oil |
| 0.2 g | of PPG-1-PEG-9 lauryl glycol ether |
| 0.1 g | of perfume |
| 20 g | of ethanol |
| to 100 g | water |

Figure 2:
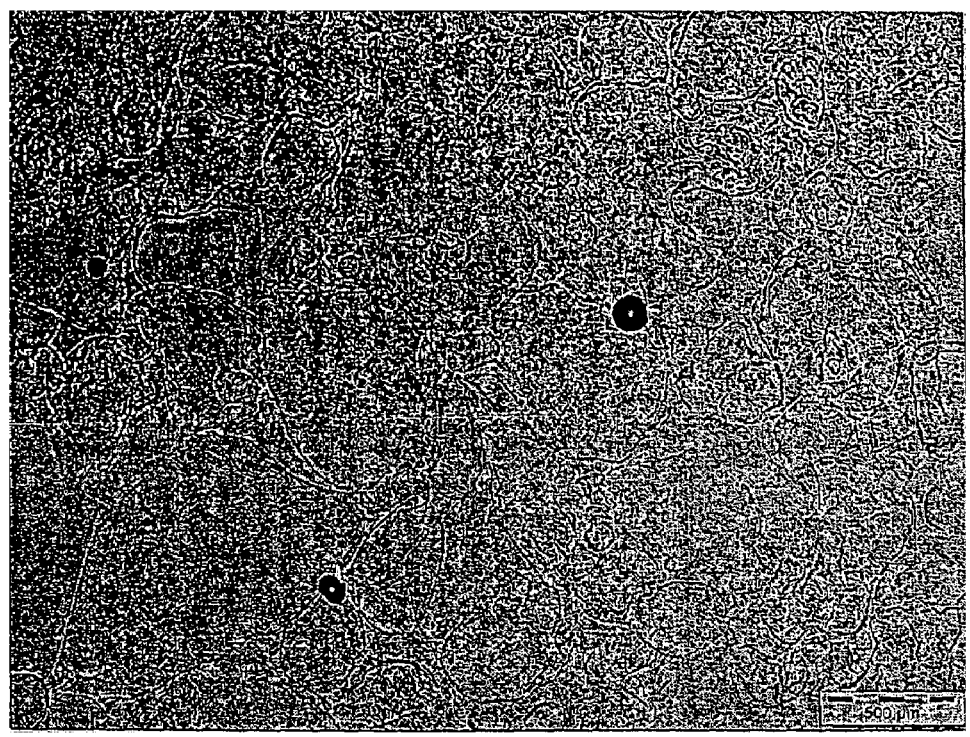
FIG. 2/3 shows a photograph of a gel of the invention (Example 2) taken in transmitted light (lens 2.5×). The gel is resting on a specimen slide under a cover glass. The thin, black lines show the outlines of the swollen polymer particles. The small, round, black objects are air bubbles.

[1] PVP = polyvinylpyrrolidone; VA = vinyl acetate; PEG = polyethylene glycol; PPG = polypropylene glycol - Translator FIG. 1/3 shows a photograph of the gel surface in reflected light (lens: 2.5×). The gel is resting on a specimen slide. FIG. 2/3 shows a photograph of the gel in transmitted light (lens: 2.5×). The gel is resting on a specimen slide under a cover glass. The thin, black lines show the outlines of the swollen polymer particles. The small, round, black objects are air bubbles.

Example 3

Hair Gel

| | |
|---|---|
| 0.6 g | of Sanwet ® 3746-5 (BASF, superabsorbing sodium polyacrylate) |
| 12 g | of glucose |
| 0.2 g | of PEG-40 hydrogenated castor oil |
| 0.2 g | of PPG-1-PEG-9 lauryl glycol ether |
| 0.1 g | of perfume |
| 15 g | of ethanol |
| to 100 g | water |

Example 4

Hair Gel

| | |
|---|---|
| 0.5 g | of Sanwet ® 3746-5 (BASF, superabsorbing sodium polyacrylate) |
| 10 g | of Luviskol ® K 30 (BASF, polyvinylpyrrolidone) |
| 0.2 g | of PEG-40 hydrogenated castor oil |
| 0.2 g | of PPG-1-PEG-9 lauryl glycol ether |

-continued

| | |
|---|---|
| 0.1 g | of perfume |
| 20 g | of ethanol |
| to 100 g | water |

Example 5

Luster-Imparting Hair Gel

| | |
|---|---|
| 0.7 g | of Sanwet ® 3746-5 |
| | (BASF, superabsorbing sodium polyacrylate) |
| 10 g | of glycerol |
| 0.2 g | of PEG-40 hydrogenated castor oil |
| 0.2 g | of PPG-1-PEG-9 lauryl glycol ether |
| 0.1 g | of perfume |
| 20 g | of ethanol |
| to 100 g | water |

Example 6

Comparative Example

| | |
|---|---|
| 0.8 g | of Carbomer (crosslinked polyacrylic acid thickener) |
| 0.59 g | of aminomethylpropanol |
| 2.0 g | of polyvinylpyrrolidone |
| 1.72 g | of glycerol |
| 0.8 g | of Polysorbate 40 |
| 0.2 g | of PPG-1-PEG-9 lauryl glycol ether |
| 0.2 g | of perfume |
| 14.25 g | of ethanol |
| to 100 g | water |

Figure 3:
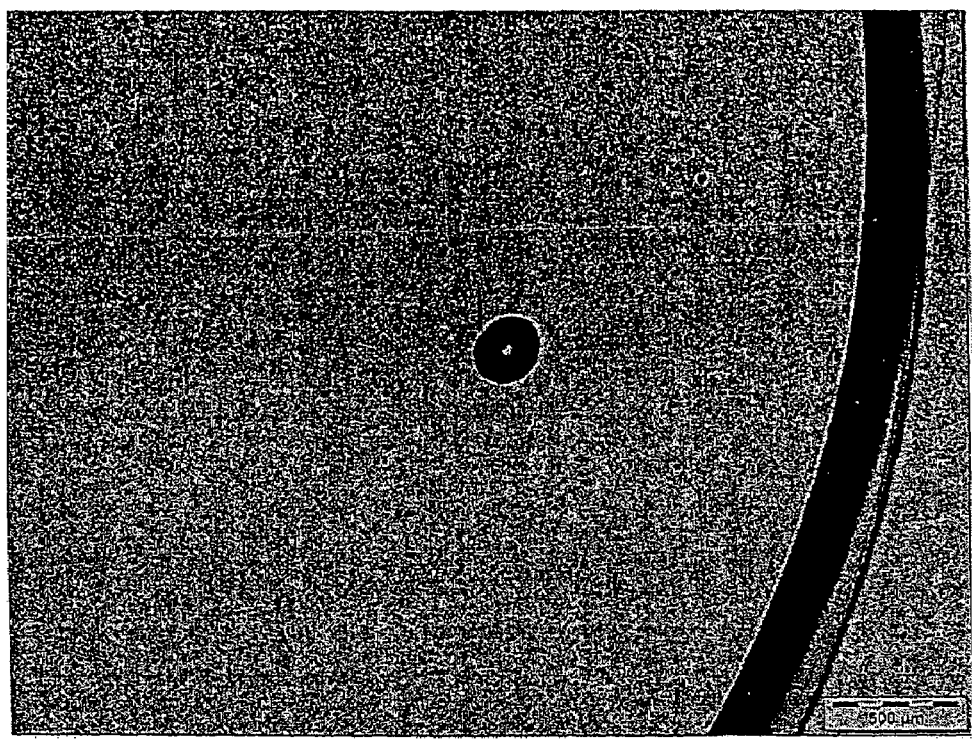
FIG. 3/3 shows a photograph of a conventional gel not according to the invention (comparative example) with completely dissolved gel former, taken in transmitted light (lens 2.5×). The gel rests on a specimen slide under a cover glass. The small, round, black objects are air bubbles.

FIG. 3/3 shows a photograph of the reference gel with completely dissolved gel former, taken in transmitted light (lens: 2.5×). The gel rests on a specimen slide under a cover glass. The small, round, black objects are air bubbles.

Example 7

Styling Gel

| | |
|---|---|
| 0.7 g | of Norsocryl ® XFS |
| | (Elf Atochem, superabsorbing sodium polyacrylate) |
| 7.5 g | of Luviskol ® VA 64 (BASF, PVP/VA copolymer) |
| 0.2 g | of PEG-40 hydrogenated castor oil |
| 0.2 g | of PPG-1-PEG-9 lauryl glycol ether |
| 0.1 g | of perfume |
| 15 g | of ethanol |
| to 100 g | water |

Example 7

Hair End Protection for Permanent Wave Treatment

| | |
|---|---|
| 2 g | of Hysorb ® E 1290-00 |
| | (BASF, superabsorbing sodium polyacrylate) |
| to 100 g | water |

Normal, not previously damaged hair was washed and towel-blotted. The gel of the above-indicated composition obtained by stirring or shaking was applied portionwise (1 g) to the ends of the hair separated into strands. The hair was then wound in the usual manner onto permanent wave curlers with a diameter of 6 millimeters.

The hair was then uniformly moistened with the following hair-shaping agent:

| | |
|---|---|
| 10.5 g | of thioglycolic acid, 80% |
| 5.0 g | of ammonium hydrogen carbonate |
| 1.0 g | of ammonia, 25% |
| 1.5 g | of cationic polymer |
| 1.0 g | of dissolution promoter (isooctylphenol, ethoxylated with 10 moles of ethylene oxide) |
| 0.4 g | of perfume |
| to 100 g | water |

After an exposure time of 15 minutes, the hair was thoroughly rinsed with water and then subjected to oxidative post-treatment with 80 grams of 3% aqueous hydrogen peroxide solution. After removing the curlers, the hair was once again rinsed with water, styled into a water wave and then dried. At the end of the waving procedure, the wave appearance was uniform from hair root to hair end.

Example 8

Hair End Protection for Permanent Wave Treatment

| | |
|---|---|
| 0.7 g | of Sanwet ® 3746-5 |
| | (BASF, superabsorbing sodium polyacrylate) |
| 0.2 g | of PEG-40 hydrogenated castor oil |
| 0.2 g | of PPG-1-PEG-9 lauryl glycol ether |
| 0.1 g | of perfume |
| 20 g | of ethanol |
| to 100 g | water |

A permanent wave end paper was coated with this composition. The ends of the hair to be treated, arranged in strands, were placed in the end paper. The permanent wave treatment described in Example 7 was then applied. The permanent wave treatment by use of the coated end paper provided extreme protection of the hair ends which resulted in a long-lasting, gentle hair wave curve.

Example 9

Hair End Protection for Permanent Wave Treatment

| | |
|---|---|
| 1.2 g | of Hysorb® E 1291-00 (BASF, superabsorbing sodium polyacrylate) |
| 10 g | of glucose |
| 0.2 g | of PEG-40 hydrogenated castor oil |
| 0.2 g | of PPG-1-PEG-9 lauryl glycol ether |
| 0.1 g | of perfume |
| 5 g | of ethanol |
| to 100 g | water |

A permanent wave end paper was coated with this composition. The ends of the hair to be treated, arranged in strands, were placed in the end paper. The permanent wave treatment described in Example 7 was then applied. The permanent wave treatment by use of the coated end paper provided extreme protection of the hair ends which resulted in a long-lasting, gentle hair wave curve.

Example 10

Hair End Protection for Permanent Wave Treatment

| | |
|---|---|
| 1.0 g | of Sanwet® 3746-5 (BASF, superabsorbing sodium polyacrylate) |
| to 100 g | water |

The gel obtained by stirring or shaking was applied portionwise (1 g) onto the ends of hair separated into strands. The hair was then wound onto permanent wave curlers and subjected to permanent waving, as described in Example 7. At the end of the waving procedure, the wave appearance was uniform from hair root to hair end.

Example 11

Comparative Test

In a side-by-side test on the same scalp, the left half of the head was subjected to permanent waving by use of conventional end paper. On the right half, water-swollen superabsorber Hysorb® E 1290-00, 1 wt. % in water, was used for hair-end protection in the manner indicated hereinabove.

The result of the waving showed that on the right half of the head which had been treated with the gel the curling of the hair ends had a clearly larger radius.

Example 12

Comparative Test

In a side-by-side test on the same scalp, strongly predamaged hair on the left half of the head was subjected to permanent waving by use of common end papers. On the right side of the head, water-swollen superabsorber (Hysorb® E 1290-00), 1 wt. % in water, was used for hair-end protection in the above-indicated manner.

It was clearly evident on both moist and dry hair that on the right side the use of the gel of the invention provided a more uniform wave appearance from the roots to the ends.

The invention claimed is:

1. A cosmetic preparation consisting of a gel, wherein said gel consists of:
    from 0.05 to 20 wt. % of at least one superabsorbing polymer selected from the group consisting of acrylic acid polymers and methacrylic acid polymers;
    from 0.1 to 30 wt. % of at least one nonionic film-forming, hair-fixing polymer;
    water;
    up to 30 wt. % of alcohol; and
    at least one cosmetic additive ingredient selected from the group consisting of thickeners, surfactants, perfume oils, opacifiers, pearly luster-imparting agents, bactericides, fungicides, buffers, tinting agents, hair-care agents and physiologically tolerated volatile and non-volatile silicone oils;
    wherein said gel contains from about 0.2 to 3.0 wt. % of at least one of said thickeners when said at least one of said thickeners is present in said gel; said gel contains from 0.1 to 15 wt. % of at least one of said surfactants when said at least one of said surfactants is present in said gel; said gel contains from 0.1 to 0.5 wt. % of at least one of said perfume oils when said at least one of said perfume oils is present in said gel; said gel contains from about 0.2 to 5.0 wt. % at least one of said opacifiers when said at least one of said opacifiers is present in said gel; said gel contains from about 1.0 to 10 wt. % of at least one of said pearly luster-imparting agents when said at least one of said pearly luster-imparting agents is present in said gel; said gel contains from 0.01 to 1.0 wt. % of at least one of said bactericides and fungicides when said at least one of said bactericides and fungicides is present in said gel; said gel contains from 0.1 to 1.0 wt. % of at least one of said buffers when said at least one of said buffers is present in said gel; said at contains from about 0.1 to 1.0 wt. % of at least one of said tinting agents when said at least one of said tinting agents is present in said gel; and said gel contains from 0.1 to 5.0 wt. % of at least one of said hair-care agents when said at least one of said hair-care agents is present in said gel; and said gel contains from 0.05 to 20 wt. % of at least one of said physiologically tolerated volatile and non-volatile silicone oils when said at least one of said silicone compounds is present in said gel; and
    wherein said at least one superabsorbing polyacrylate polymer is present in the form of undissolved, water-swollen gelled particles with an average particle diameter of from 20 to 2000 μm.

2. The cosmetic preparation as defined in claim 1, containing from 0.1 to 2 wt. % of said at least one superabsorbing polyacrylate polymer.

3. The cosmetic preparation as defined in claim 1, wherein said at least one nonionic film-forming, hair-fixing polymer comprises at least one monomer and said at least one monomer is selected from the group consisting of vinyl pyrrolidone, vinylcaprolactam, vinyl acetate, vinyl alcohol, acrylamides, methacrylamides, alkylacrylamides, dialkylacrylamides, alkylmethacrylamides, dialkylmethacrylamides, alkyl acrylates, alkyl methacrylates, propylene glycol and ethylene glycol, and wherein the alkyl groups in the at least one monomer are $C_1$- to $C_7$-alkyl groups.

4. The cosmetic preparation as defined in claim 1, wherein said at least one nonionic film-forming, hair-fixing polymer is polyvinyl pyrrolidone; a copolymer of vinyl pyrrolidone and vinyl acetate; a terpolymer of vinyl pyrrolidone, vinyl acetate and vinyl propionate; a polyacrylamide, a polyvinyl alcohol, or a polyethyleneglycol/polypropylene glycol copolymer.

5. The cosmetic preparation as defined in claim 1, wherein said at least one nonionic film-forming, hair-fixing polymer is polyvinyl pyrrolidone, polyvinyl caprolactam, or polyvinyl pyrrolidonelvinyl acetate copolymer.

6. The cosmetic preparation as defined in claim 1, wherein said gel has a viscosity of from 500 to 3000 mPa·s at a temperature of 25 ° C. under a shear gradient of 0.5 to 1400 $s^{-1}$.

7. The cosmetic preparation as defined in claim 1, which reversibly forms a grainy, uneven, light-scattering surface at an interface with a gaseous substance and a smooth, level, non-light-scattering surface at an interface with a solid.

8. The cosmetic preparation as defined in claim 1, wherein said alcohol is a lower alcohol with 1 to 4 carbon atoms.

9. A cosmetic preparation consisting of a gel that reversibly forms a grainy, uneven, light-scattering surface at an interface with a gaseous substance and a smooth, level, non-light-scattering surface at an interface with a solid;
wherein said gel consists of:
from 0.05 to 2 wt. % of a superabsorbing sodium polyacrylate polymer;
from 0.1 to 30 wt. % of at least one nonionic film-forming, hair-fixing polymer;
water
up to 30 wt. % of alcohol; and
at least one cosmetic additive ingredient selected from the group consisting of thickeners, surfactants, perfume oils, opacifiers, pearly luster-imparting agents, bactericides, fungicides, buffers, tinting agents, hair-care agents and physiologically tolerated volatile and non-volatile silicone oils;
wherein said gel contains from about 0.2 to 3.0 wt. of at least one of said thickeners when said at least one of said thickeners is present in said gel; said gel contains from 0.1 to 15 wt. % of at least one of said surfactants when said at least one of said surfactants is present in said gel; said gel contains from 0.1 to 0.5 wt. % of at least one of said perfume oils when said at least one of said perfume oils is present in said gel; said gel contains from about 0.2 to 5.0 wt. % at least one of said opacifiers when said at least one of said opacifiers is present in said gel; said gel contains from about 1.0 to 10 wt. % of at least one of said pearly luster-imparting agents when said at least one of said pearly luster-imparting agents is present in said gel; said gel contains from 0.01 to 1.0 wt. % of at least one of said bactericides and fungicides when said at least one of said bactericides and fungicides is present in said gel; said gel contains from 0.1 to 1.0 wt. % of at least one of said buffers when said at least one of said buffers is present in said gel; said gel contains from about 0.1 to 1.0 wt. % of at least one of said tinting agents when said at least one of said tinting agents is present in said gel; and said gel contains from 0.1 to 5.0 wt. % of at least one of said hair-care agents when said at least one of said hair-care agents is present in said gel; and said gel contains from 0.05 to 20 wt. % of at least one of said physiologically tolerated volatile and non-volatile silicone oils when said at least one of said silicone compounds is present in said gel; and
wherein said superabsorbing sodium polyacrylate polymer is present in the form of undissolved, water-swollen gelled particles with an average particle diameter of 200 μm or less; and
wherein said gel has a viscosity of from 500 to 3000 mPa·s at a temperature of 25° C. under a shear gradient of 0.5 to 1400 $s^{-1}$.

\* \* \* \* \*